(12) United States Patent
Payne

(10) Patent No.: US 7,092,084 B2
(45) Date of Patent: Aug. 15, 2006

(54) SYSTEM AND METHOD FOR SENSING A CHARACTERISTIC OF A FLUID AND RELATED APPARATUS

(75) Inventor: Fred A. Payne, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 317 days.

(21) Appl. No.: 10/201,117

(22) Filed: Jul. 23, 2002

(65) Prior Publication Data

US 2004/0017569 A1    Jan. 29, 2004

(51) Int. Cl.
*G01N 1/10*    (2006.01)
(52) U.S. Cl. ....................... 356/246; 356/440
(58) Field of Classification Search ............... 356/244, 356/246, 440; 422/102; 436/164
See application file for complete search history.

(56) References Cited

U.S. PATENT DOCUMENTS

| | | | | |
|---|---|---|---|---|
| 3,480,398 A | * | 11/1969 | Hamilton | 422/102 |
| 3,552,855 A | * | 1/1971 | Crosswy et al. | 356/28 |
| 3,869,214 A | * | 3/1975 | Egli et al. | 356/246 |
| 4,634,576 A | * | 1/1987 | Galle et al. | 422/102 |
| 4,668,636 A | * | 5/1987 | Ringrose et al. | 436/164 |
| 4,779,003 A | * | 10/1988 | Tatsuno | 250/575 |
| 5,172,193 A | | 12/1992 | Payne et al. | |
| 5,414,195 A | * | 5/1995 | Peterson et al. | 588/1 |
| 5,572,320 A | * | 11/1996 | Reintjes et al. | 356/335 |
| 5,905,271 A | | 5/1999 | Wynn | |
| 6,052,184 A | * | 4/2000 | Reed | 356/338 |
| 6,507,401 B1 | * | 1/2003 | Turner et al. | 356/436 |
| 6,707,556 B1 | * | 3/2004 | Turner et al. | 356/436 |

FOREIGN PATENT DOCUMENTS

| | | | | |
|---|---|---|---|---|
| DE | 3806286 | * | 8/1989 | |
| JP | 402028538 A | * | 1/1990 | |
| JP | 402249951 A | * | 10/1990 | |

OTHER PUBLICATIONS

Daritek, "The Better Solution for Cost Control: Model 116/AF16," www.daritek.com.
Wedgewood Technology Incorporated, "Model AF10—Single Beam Absorbance In-line Sensor," www.wedgewoodtech.com.

* cited by examiner

*Primary Examiner*—Hoa Q. Pham
(74) *Attorney, Agent, or Firm*—King & Schickli, PLLC

(57) ABSTRACT

An apparatus for intended use in measuring, sensing, or detecting a characteristic of a fluid, such as a liquid food product, is disclosed. The apparatus includes a body having a pocket for positioning adjacent to the opening in a pipe or like structure for receiving a portion of a fluid therein. In one possible use, a first optical medium, such as an optical fiber, transmits light from a source toward a portion of the fluid flow entering the pocket. Light received by one or more optical mediums positioned in backscatter, sidescatter, or transmission configurations relative to the first optical medium is detected by a corresponding sensor or detector. Using the output of this sensor or detector, an optical characteristic of the fluid may be measured. An overall system using the apparatus and related method for detecting an optical characteristic of a fluid are also disclosed.

25 Claims, 4 Drawing Sheets

SYSTEM AND METHOD FOR SENSING A CHARACTERISTIC OF A FLUID AND RELATED APPARATUS

TECHNICAL FIELD

The present invention relates to the art of sensing, detecting, or measuring a characteristic of a fluid, such as a liquid food product. More particularly, the present invention relates to an improved apparatus for use in detecting light transmitted through or reflected by a fluid flowing along a pipeline, along with a system incorporating the apparatus and a related method.

BACKGROUND OF THE INVENTION

The food, pharmaceutical, and chemical industries rely heavily on the use of devices for measuring, sensing, or detecting characteristics of a fluid, such as a liquid containing particles. For example, optical sensors are frequently used to detect characteristics of milk in an effort to determine the amount of a particular component present, such as milkfat or casein. The amount of the component detected or sensed then determines whether the fluid meets a certain criteria before undergoing further processing or whether it is suitable for a particular use (i.e., in the case of milk, whether it is suitable for making a particular type, grade, or variety of cheese). Such devices may also be used for detecting when transitions from one fluid product to another occur in a pipeline (i.e., milk to water) or when a cleaning fluid passing through the pipeline reaches a particular level of optical clarity.

In one type of sensing arrangement, light is transmitted from a remote source to a first optical transmitter projecting directly into the stream of fluid passing through a cylindrical pipe segment forming part of a pipeline. A corresponding light receiver is positioned directly opposite the transmitter for receiving any light passing through the fluid as it flows along the pipeline. A light sensor or photodetector associated with or coupled to the receiver detects the amount of light received and generates a corresponding output signal. Using this output signal, a prediction may be made regarding the type of fluid present and/or the amount of a particular substance (e.g., milkfat particles, casein, etc.) in the fluid moving through the pipeline.

While this "transmision" type of sensor arrangement generally permits taking of the desired measurements in an acceptable manner, there are several well-recognized limitations. One significant limitation is that the transmitter and receiver typically project transversely into the fluid flow from the outer wall of the pipeline. Of course, this positioning severely disrupts the fluid flow and may have a deleterious effect on the sensing accuracy. The large physical distance (path length) also limits transmission measurements to relatively clear fluids. Meaningful measurements with whole milk, cream, and other thick fluids cannot be made with the typical transmission sensor. This problem has been addressed by firms such as Wedgewood and Daritek by fabricating lenses that protrude into the fluid. Daritek lists an optical path length (OPC) of 5, 100, and 20 millimeters for their sensor, and Wedgewood explains that custom path lengths are available. However, one of the technical problems with a protruding optical means having a short path length is stability. For example, vibrations, and especially thermal movement of the wall, results in relatively large displacement in the path length. This increases signal error, especially in highly turbid fluids. The protrusion of an optical means into the flow stream may also inhibit fluid flow.

In an effort to prevent this disruption, others have proposed positioning one or more lenses in the outer wall of the pipeline to separate the transmitter and receiver from the fluid flow. However, this increases the path length and complicates the arrangement. Perhaps more importantly, it also prevents the light path distance between the transmitter and the receiver from being easily adjusted.

Accordingly, a need is identified for an improved apparatus for use in measuring, sensing, or detecting a characteristic of a fluid. The apparatus would be inexpensive to manufacture and would be readily adaptable for use with existing fluid vessels, containers, or pipelines. Furthermore, it would allow for the adjustable positioning of one or more devices or units for transmitting/receiving energy to the fluid without creating any significant disturbance therein. Moreover, the apparatus would allow for mounting of the transmitter/receiver in not only a backscatter or transmission configuration, but also in a sidescatter configuration. This would possibly allow for more precise measurements to be taken, including in dense fluids. Overall, the apparatus would result in a significant improvement in terms of reliability and ease of use, especially as compared to the prior art optical sensing arrangement described above.

SUMMARY OF THE INVENTION

In accordance with a first aspect of the invention, an apparatus for the intended use in receiving at least one medium, such as an optical fiber, for transmitting energy to a fluid in a pipe or other vessel having an outer wall with an opening formed therein is provided. The apparatus comprises a body for positioning adjacent to the opening. The body includes a pocket for receiving a portion of the fluid passing through the opening. The pocket is at least partially defined by a first sidewall having a first passage adapted for receiving at least a portion of the at least one medium such that energy transmitted therethrough reaches the portion of the fluid in the pocket.

In one embodiment, the at least one medium is a first optical fiber for transmitting light from a light source to the fluid entering the pocket. Preferably, the first optical fiber is associated with a first fiber optic unit including the light source and the body includes a first auxiliary passage for receiving one or more transmission lines coupled to the first fiber optic unit. A second passage for receiving at least a portion of a second optical medium may be formed in a second sidewall partially defining the pocket such that light transmitted by the first optical medium into the portion of the fluid in the pocket is received by the second optical medium. The first and second passages may be oriented for positioning the first and second optical mediums in either a transmission configuration or a sidescatter configuration. Also, a third sidewall partially defining the pocket may include a third passage adapted for receiving at least a portion of a third optical medium for receiving light transmitted to the portion of the fluid flow entering the pocket by the first optical medium. The second optical medium may be associated with a second fiber optical unit and the body may further include a second auxiliary passage for receiving one or more transmission lines coupled thereto.

Preferably, the body is a single piece of material, the first and second sidewalls are opposed, and the first and second passage are formed using a single tool during a continuous machining process. This is done to ensure proper alignment among the first and second optical mediums when positioned in a transmission configuration. The pocket is partially defined by a generally U-shaped bottom wall. As should be appreciated, this shape or contour promotes smooth fluid flow and easy cleaning.

In accordance with a second aspect of the invention, a system for detecting an optical characteristic of a fluid flowing through a pipeline is provided. The system comprises a pipe segment for forming a portion of the pipeline. The segment includes an outer wall having an opening for communicating with a pocket for receiving a portion of the fluid flow. The pocket is at least partially defined by a first sidewall having a first passage formed therein. The system further includes a light source and a first optical medium positioned at least partially in the first passage for transmitting light from the light source to the fluid flow in the pocket. A second optical medium capable of receiving light transmitted through or reflected by the portion of the fluid flow in the pocket is also provided. A detector is coupled to the second optical medium for detecting the light received by the second optical medium.

In one embodiment, the second optical medium is positioned at least partially in the first passage to create at least a backscatter configuration. The pipe segment will include a second sidewall partially defining the pocket. The second sidewall may include a second passage adapted for at least partially receiving a second optical medium. It is thus possible to orient the first and second optical mediums in a sidescatter configuration or a transmission configuration. Furthermore, the pipe segment may include a third sidewall partially defining the pocket and including a third passage adapted for receiving a third optical medium. The system may further include a second detector associated with the third optical medium for detecting light transmitted to the fluid in the pocket. In the case where the first and second optical mediums are in a transmission configuration, the third optical medium may be mounted in a sidescatter configuration. In this case, a fourth optical medium oriented in a backscatter configuration relate to the first optical medium may also be provided.

Preferably, the third sidewall is a generally U-shaped bottom wall that promotes the smooth flow of fluid through the pocket. The pocket may be formed in a separate piece of material attached directly to the pipe segment over the opening formed therein. The material may include first and second auxiliary passages for receiving one or more transmission lines coupled to first and second fiber optical units associated with the first and second optical mediums, respectively.

In one embodiment, the first optical medium is held in a first bore formed in a first sleeve adapted for positioning in the first passage. The sleeve includes a distal tip and an oversized body. The corresponding passage is adapted for receiving the sleeve such that the distal tip projects into the pocket.

In accordance with a third aspect of the invention, a method of sensing a characteristic of a fluid in a pipe or other vessel having an outer wall with an opening therein is provided. The method comprises: (1) providing a pocket adjacent to the opening for receiving a portion of the fluid; (2) transmitting energy to the portion of the fluid; and (3) detecting the amount of energy transmitted through or reflected by the portion of the fluid. Preferably, the transmitting step includes transmitting light through a first optical fiber. The detecting step may include detecting light reflected from the fluid to a second optical fiber, including by detecting light received by second, third, or fourth optical fibers oriented in backscatter, sidescatter, and transmission configurations, respectively.

BRIEF DESCRIPTION OF THE DRAWINGS

FIG. 2a is an enlarged, cutaway front view of the distal tip of a fiber optic unit adapted for backscatter measurement;

DETAILED DESCRIPTION OF THE PREFERRED EMBODIMENTS

Figure 1:
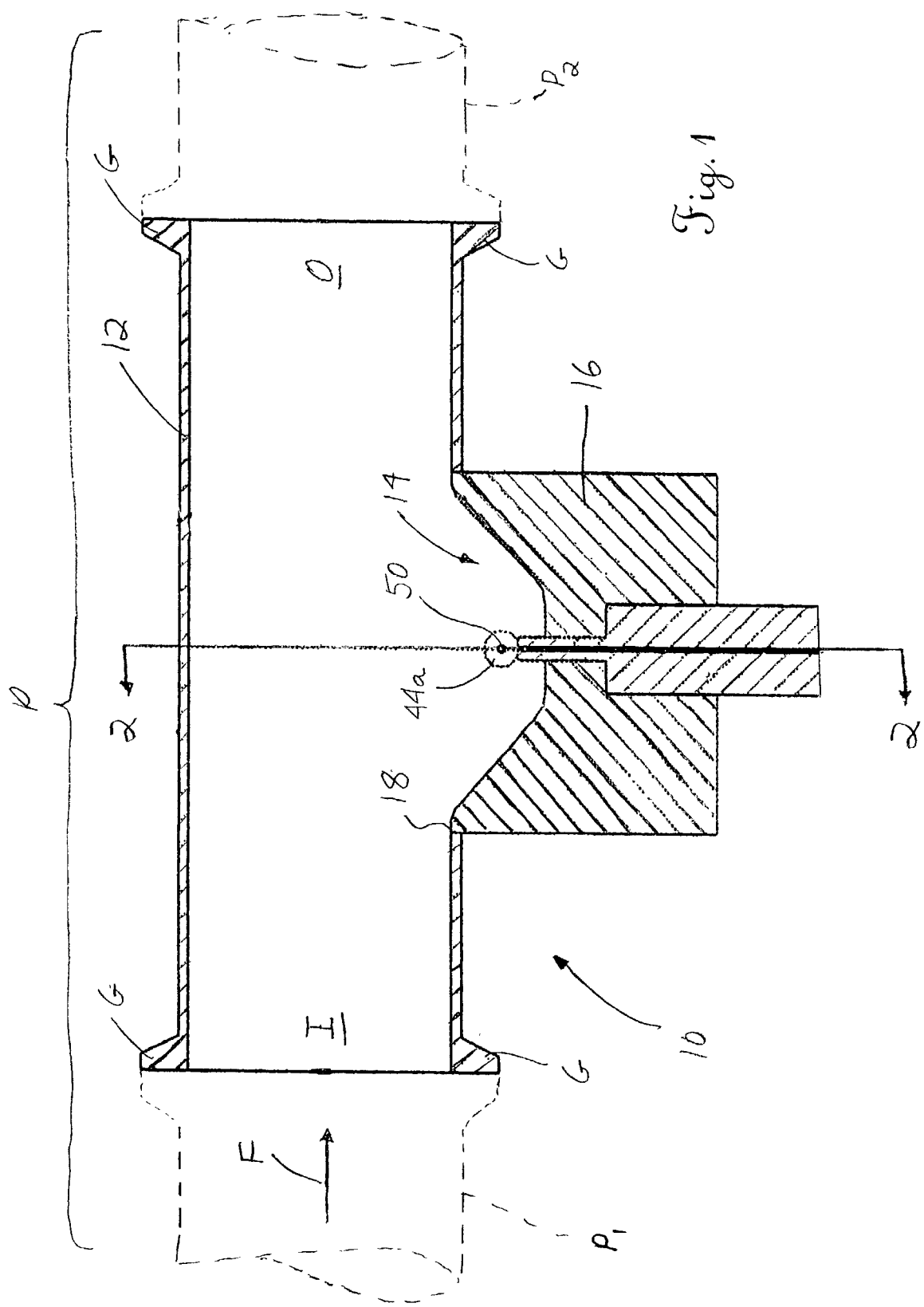
FIG. 1 is a cross-sectional side view of the apparatus of the present invention in use on a pipeline along which a fluid is flowing.

Reference is now made to FIG. 1, which shows a pipe segment 10 including the apparatus of the present invention. The segment 10 includes an inlet I for receiving a fluid F, such as a liquid food product (e.g., milk) flowing from an upstream pipe segment $P_1$ in a pipeline P and an outlet O for discharging the flow to a downstream pipe segment $P_2$. The portion of the segment 10 for receiving the fluid F includes an outer wall 12. The outer wall 12 may have a substantially circular cross-section, although other cross-sectional shapes can be used as necessary or desired for a particular application. Oversized annular flanges G may be provided at the ends of the cylindrical wall 12 for mating with corresponding flanges on pipe segments $P_1$, $P_2$. As should be appreciated, these flanges G when mated with the corresponding flanges on the adjacent pipe segments $P_1$, $P_2$ create an interface capable of receiving a clamp or other attachment means (not shown) such that a secure, fluid-impervious connection is formed. In the case of a clamp, it may also be desirable to use a seal or sealing substance at the interface between the flanges.

In accordance with a first aspect of the invention, a pocket 14 is provided adjacent to the pipe segment 10 for receiving a portion of the fluid F flowing along the pipeline P. In the preferred embodiment, as shown in FIG. 1, the pocket 14 is formed as a cavity in a body 16 of material secured adjacent to an opening 18 in the outer wall 12 of the pipe segment 10. The body 16, which is preferably formed of a durable, corrosion resistant material, such as stainless steel, may be secured directly to the outer wall 12 of the pipe segment 10, such as by welding or other secure means of attachment. Consequently, fluid F flowing along the pipeline P automatically enters and flows through the pocket 14. As discussed further in the description that follows, the pocket 14 is preferably provided with a smooth contour that promotes the smooth flow of fluid F therethrough.

Figure 2:
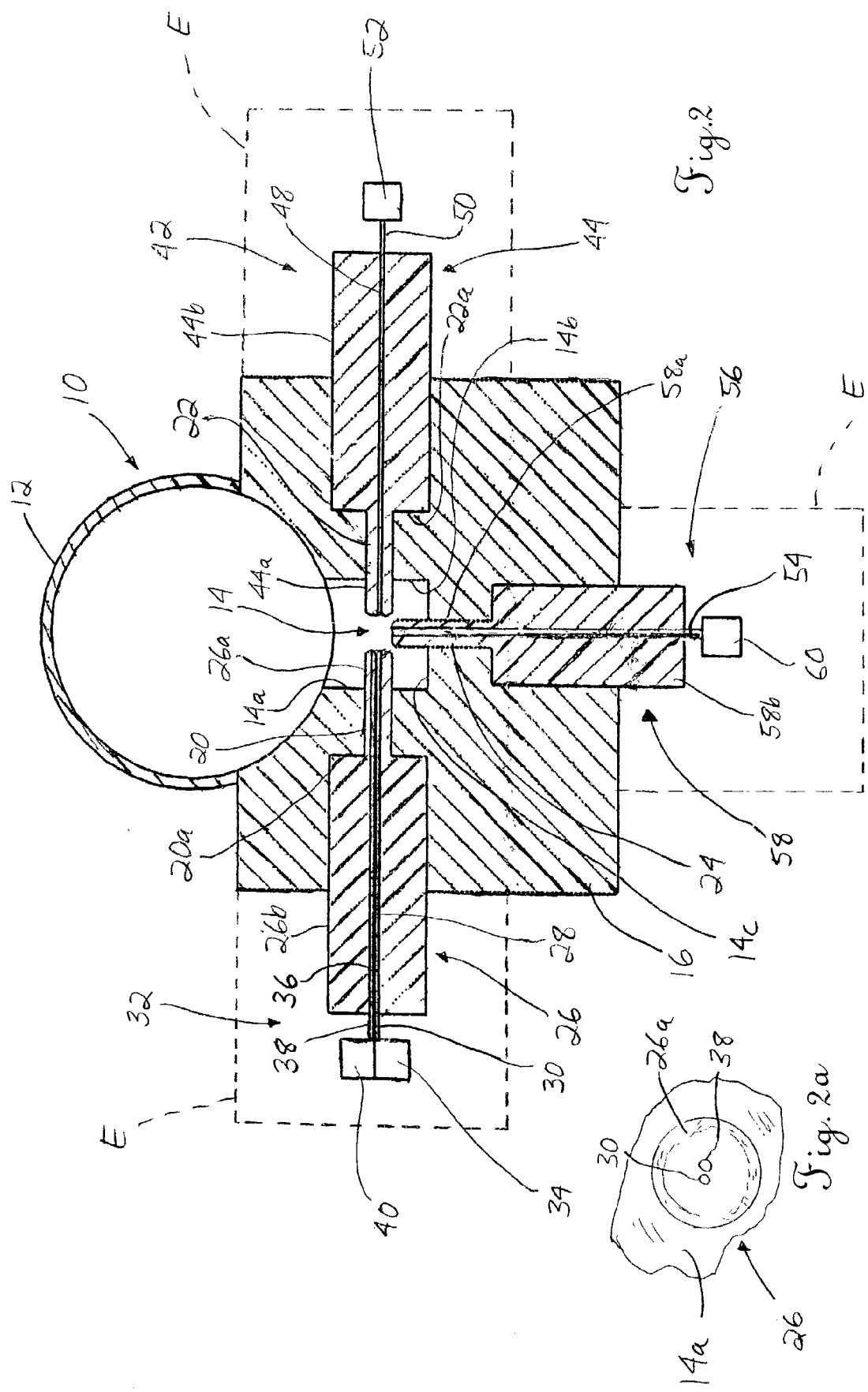
FIG. 2 is a cross-sectional view taken along line 2—2 of FIG. 1, and depicts the use of three fiber optic units with the apparatus, which makes it possible to take backscatter, transmission, or sidescatter measurements.

As perhaps best understood with reference to FIG. 2, which is taken along line 2—2 of FIG. 1, the body 16 includes at least one, and preferably a plurality of passages 20, 22, 24, each for receiving at least one optical medium capable of transmitting or receiving light. Specifically, first referring to the left hand side of FIG. 2 which shows a preferred embodiment of the invention, the first passage 20 is adapted to receiving a sleeve 26 having at least one bore 28. At least one optical fiber 30 (such as, for example, a 400 micron specialty fiber available from FiberGuide Industries) is at least partially positioned in the bore 28. In this preferred embodiment, the sleeve 26 includes a distal tip 26a that projects through a first vertically extending sidewall 14a partially defining the pocket 14. Thus, the distal tip 26a advantageously does not project directly into the fluid F flowing along the pipeline P. Consequently, the disruption in the flow is minimized.

Preferably, the distal tip 26a is smaller in size than the remainder portion or body 26b of the sleeve 26 (which is shown as being cylindrical) and the passage 20 for receiving the sleeve 26 is shaped accordingly. Consequently, a step 20a is formed in the passage 20 to provide a seating surface for the flat face on the body 26b of the sleeve 26 surrounding the base of the distal tip 26a. As mentioned below, a seal (not shown) is preferably provided by an O-ring installed into the distal tip 26a and is compressed between it and the seating surface. As shown be appreciated, by changing the length of the distal tip 26a and/or adjusting the position (depth) of the portion of the passage 20 for receiving the body 26b of the sleeve 26, the axial distance that the optical fiber 30 projects into the pocket 14 may be adjusted as necessary or desired for a particular application (such as when a transmission configuration is used, as described further below).

In the illustrated embodiment, the sleeve 26 together with the at least one optical fiber 30 may be considered to form part of a first fiber optic unit 32. In one possible embodiment, this first fiber optic unit 32 further includes a light source, such as an LED 34 (shown schematically in FIG. 2), adapted for transmitting light energy through the corresponding optical fiber 30 to the fluid F entering the pocket 14. An example of an LED that may be used as part of the present system is a Hamamatsu Infrared GaAIAs LED Model L2791-02 capable of outputting light at 880 nm. As should be appreciated, the wavelength can be adjusted or changed as desired or necessary for a particular application. For example, during experimentation, it was discovered that blue light worked better than infrared light when used for detecting the difference between water and a sugar solution.

When used in a backscattering configuration, the sleeve 26 may include a second bore 36 extending essentially parallel to the first bore 28 for receiving a second optical fiber 38 coupled to a light sensor or photodetector 40 (also shown schematically in FIG. 2; see FIG. 2a, which is a front view of the distal tip 26a of the sleeve 26 having adjacent, generally parallel bores 28, 36 for receiving the top optical fibers 30, 38). In this arrangement, light transmitted through the first optical fiber 30 and reflected by the fluid F may be received by the second optical fiber 38 and transmitted to the first detector 40. Output signals taken from the detector 40 can then be used to determine certain characteristics of the fluid, as is well known in the art (see, e.g., my prior U.S. Pat. No. 5,172,193, the disclosure of which is incorporated herein by reference). One example of a detector 40 that may be used is a Texas Advantaged Optical Solutions (TAOS) TSL 235 photodetector.

Instead of or in addition to providing a backscatter configuration, the body 16 may also be adapted for receiving another, different optical fiber positioned in a transmission configuration. Like the first optical fiber 30, the second optical fiber 50 may be form part of a second fiber optic unit 42 that includes a sleeve 44 having a distal tip 44a and a body 44b. A passage 22 is provided in the body 16 for receiving the sleeve 44 of the second unit 42. The positioning is such that the distal tip 44a projects through a second vertically extending sidewall 14b defining the pocket 14, opposite the first sidewall 14a thereof, while the flat face of the oversized body 44b of the sleeve 44 rests on step 22a. The sleeve 44 includes a bore 48 for receiving the third optical fiber 50 coupled to or associated with a light sensor or photodetector 52 also forming part of the second fiber optic unit 42. Hence, light passing through the first optical fiber 30 and transmitted through the fluid F may reach the third optical fiber 50, which transmits the light to the sensor/detector 52. An outputs signal generated by the detector 52 may then be interpreted to evaluate the type of fluid F passing along the pipeline P and through the pocket 14 (e.g., milk, fruit juice, etc.) or a certain characteristic thereof (e.g., in the case of milk, fat or hey content) based on the amount of light transmitted.

To achieve accurate measurements using the transmission configuration, the portions of each passage 20, 22 for receiving the corresponding optical medium and, more particularly, the distal tip 26a, 44a of the sleeve 26, 44 forming parts of the first and second fiber optic units 32, 42 must be closely aligned in the radial direction. As should be appreciated, using the arrangement described above and shown in the drawing figures allows for near perfect alignment to be easily achieved, since the portion of the passage for receiving the distal tips 26a, 44a of the sleeves 26, 44 may be formed by drilling or otherwise boring a continuous hole through the body 16 during a single pass. By doing so, there is no chance for misalignment between the portions of the passages 20, 22 for receiving the distal tips 26a, 44a, which of course helps to ensure alignment among the optical fibers 30, 50 when positioned in a transmission configuration. The interface between the bodies 26b, 44b of the sleeves 26, 44 and the adjacent oversized portion of the passages 20, 22 also helps to insure that the proper radial positioning for the corresponding optical fibers 30, 50 is achieved.

As described above, the distance that the distal tip 44a of the second sleeve 44 projects or extends into the pocket 14 may be adjusted by changing its length or by changing the spacing of the sidewalls 14a, 14b. Consequently, using the present arrangement, the distance between the first and second fiber optic units, 32, 42 when in the transmission configuration (also called the "path length") may be easily adjusted. For example, when measuring characteristics of optically dense fluids (e.g., whole milk or half-and-half) using light, it may be desirable to position the opposed ends of the optical fibers 30, 38 in very close proximity (e.g., two millimeters apart). In the case where the adjustment is made by changing the length of the distal tips 26a, 44a of the corresponding sleeves 26, 44, it should be appreciated that the need for extensive retrofitting is avoided, which is advantageous from a cost and flexibility standpoint.

In addition to backscatter and transmission configurations, another aspect of the present invention is to provide a sidescatter configuration. To do so, the third passage 24 is provided for receiving an optical medium, such as optical fiber 54 (which is the fourth optical fiber, in the case where the first fiber optic unit 32 includes backscatter measurement capabilities and the second fiber optic unit 42 in mounted in the transmission position). The fourth possible optical fiber 54 may form part of a third fiber optic unit 56 including a sleeve 58 and a sensor or photodetector 60 to which the optical fiber 54 is coupled. The sleeve 58 may include a distal tip 58a and an oversized body 58b, with the corresponding passage 24 being shaped accordingly. As should be appreciated, by using the first fiber optic unit 32 and the third fiber optic unit 56 in the positions shown in FIG. 2, it is possible to detect light emitted by the first optical fiber 30, reflected by the fluid F to the side (hence, the term "sidescatter"), and received or collected by the fourth optical fiber 54 of the third fiber optic unit 56.

As shown in FIG. 2, optical cover or enclosure E may be provided over the proximal end of each fiber optic unit 32, 42, or 56. This enclosure E is preferably capable of preventing moisture or contaminants from penetrating and entering interfering with the operation of these units 32, 42, or 56. In the case where light is being used to perform the sensing, the enclosure E is preferably opaque to prevent ambient light from interfering with the operation of the corresponding detector 40, 52, 60. The enclosure E may be a cap having a threaded end (not shown) and a corresponding receiver (not shown) may be formed in the adjacent outer wall of the body 16. Alternatively, the enclosure E may be clamped to a mating portion (not shown) attached to and projecting from the corresponding sidewall of the body 16. The use of well-known types of seals or sealing techniques is also recommended at any interface with the enclosure where moisture could penetrate. Of course, other arrangements for protecting the fiber optic unit(s) are possible, depending on the cost objective and the particular use to which the apparatus of the present invention is being put.

Figure 3:
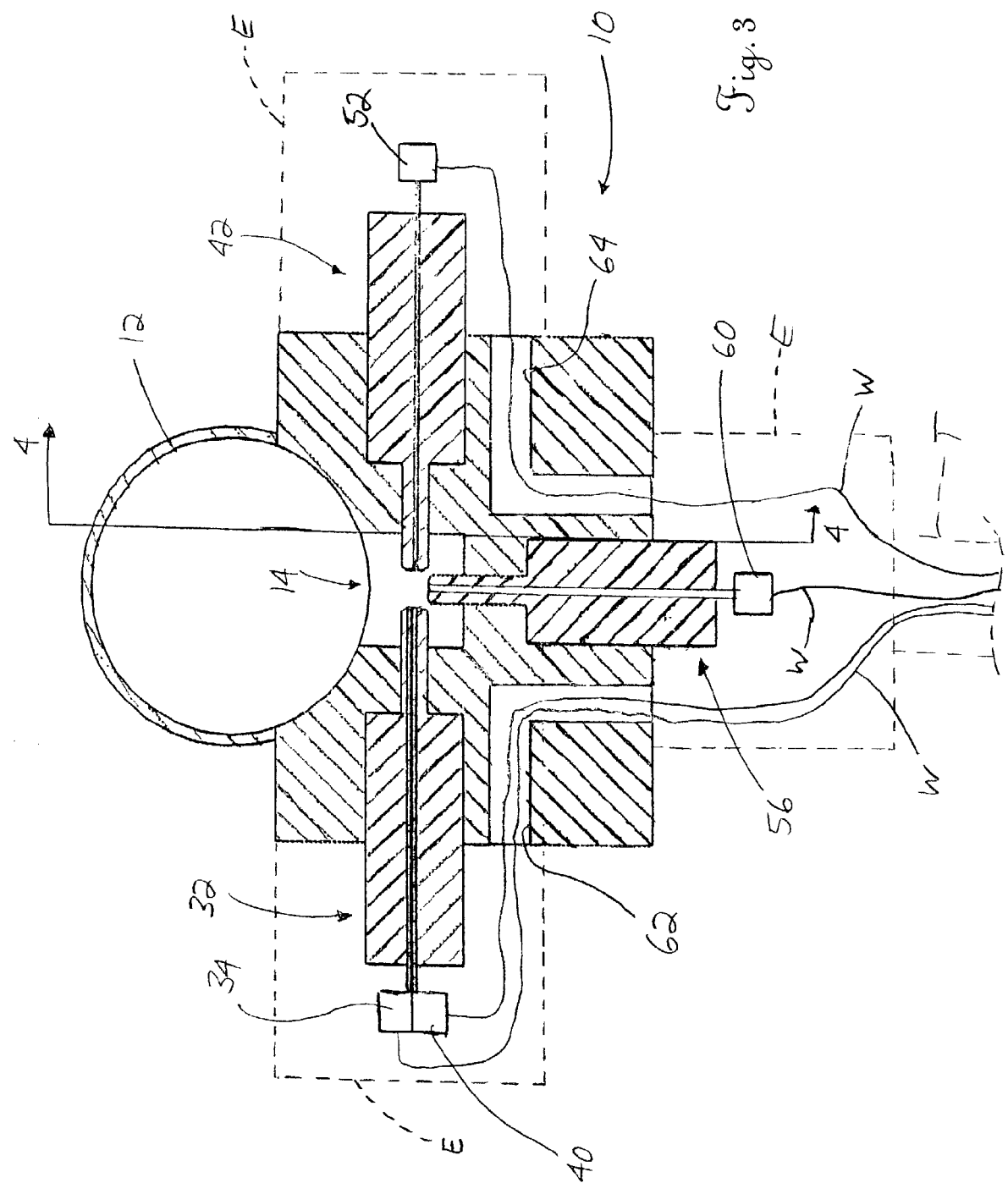
FIG. 3 is a cross-sectional view similar to FIG. 2, but showing the possible use of auxiliary passages for receiving the instrument wires connected to the fiber optic unit(s)

In cases where the enclosure E is used, it may also be desirable to allow any external connections to the fiber optic unit(s) to be routed back through the body 16 and emerge from a particular sidewall. To do so, it is possible to form additional passages in the body 16. For example, FIG. 3 shows a first auxiliary passage 62 for receiving the transmission lines or wires W (schematically shown as only one structure in FIG. 3) that supply power and receive the output signals from the light source (LED 34) and/or the sensor or detector 40, if present. In the case where the second fiber optic unit 42 and/or optical fiber 50 is present, a second auxiliary passage 64 may be provided for receiving the transmission lines or wires W from the corresponding sensor or photodetector 52. In the case where the third fiber optic unit 56 and/or optical fiber 54 is present, the wires W exiting the passages 62, 64 and any lines from the detector 60 may be routed through the common sidewall, into the corresponding enclosure E, and ultimately to a receiving structure coupled thereto, such as a tube T. The tube T guides the wires W to a remote location where the power source, computer/controller, or other means for interpreting the output signals is located. Alternatively, the wires W may feed to a socket (not shown) associated with the receiver/tube T into which a corresponding plug (not shown) from a remote controller/computer and power source fits to supply power and relay the output signals generated by the detector(s) 40, 52, or 60.

When the third fiber optic unit 56 is not present, it is possible for the first and second passages 62, 64 to merge into a third passage (not shown) that exits the body 16 adjacent to the sidewall opposite the pipe segment 12. Hence, instead of two distinct, L-shaped passages 62, 64, as shown in FIG. 3, a single T-shaped passage may be provided. The leg of this third, T-shaped passage may then communicate with a structure, such as tube T or other receiver, for receiving and guiding the wires W to a remote location. Like enclosures, the tube T may be attached directly to the corresponding wall of the body 16, such as by way of a threaded coupling, or may be clamped to a separate structure projecting therefrom. Again, the use of seals at all interfaces with the tube T is recommended.

Figure 4:
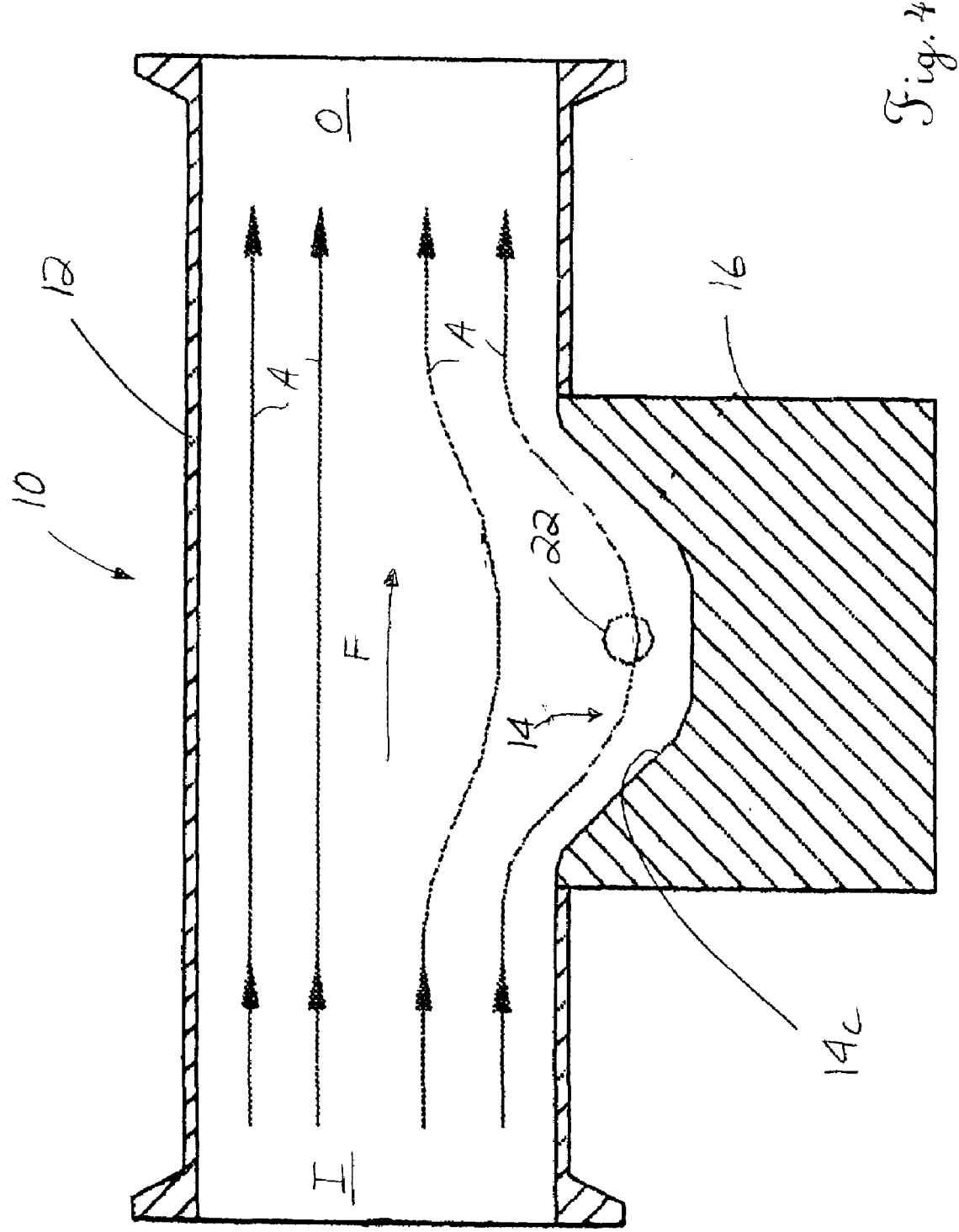
FIG. 4 is a cross-sectional side view taken along line 4—4 of FIG. 3, showing the contour of the bottom wall of the pocket in the preferred embodiment.

It is noted that FIGS. 1–3 show a preferred embodiment of the pocket 14 defined by sidewalls 14a, 14b and a bottom wall 14c havng a smooth contour to promote the smooth flow of fluid F. Specifically, as shown by the flow arrows A in FIG. 4, the bottom wall 14c of the pocket 114 is sloped adjacent to the inlet I and outlet O sides of the segment 10, preferably at an angle of less than 45° relative to the plane parallel to the centerline of the corresponding pipe segment 10 (and actually shown as being about 40° in the drawings). As indicated by the lowermost arrow A in FIG. 4, this contour promotes the smooth flow of the fluid F as it enters the pocket 14, passes any sensor/fiber optic unit(s) present, and exits the pocket. As indicated by the other arrows A, the contour of the bottom wall 14c also helps to prevent turbulence from being generated in the remainder of the fluid F flowing along the pipe segment 10. This feature creates a sanitary design that is devoid of sharp corners or crevasses where fluid or particles therein may collect over time or become trapped, even after cleaning measures are taken. Indeed, in the case of food processing, it is believed that the design of the pocket 14 shown in the drawing figures, together with the appropriate use of seals, would comply with the 3A sanitary design standards promulgated by the U.S. Department of Agriculture. As should be appreciated, this design also promotes cleaning and reduces the chances of contamination when different fluids are consecutively conveyed along the same pipeline P, as is customary. Of course, in cases where fluid turbulence and sanitation are less of a concern, the pocket 14 may be provided with a different shape, such as by changing the contour of the bottom wall 14c or the contour, slope and spacing of the opposed vertical sidewalls 14a, 14b. Moreover, while the pocket 14 is shown having a generally square or rectangular cross-sectional shape, it is possible to use other shapes as well (e.g., a cylindrical portion depending from the sidewall 12 with an end cover) without departing from the broadest aspects of the present invention.

Each sleeve 26, 44, 58 is shown as being formed of a single piece of material, such as stainless steel (preferably 304 or 316 become of the superior resistance to corrosion of each). However, it is possible to form one or more of the sleeves 26, 44, or 58 from two or more components of the same material coupled together, or even two more components of a different material coupled together. The coupling may be by way of interference fit, threaded coupling, welding, snap-fit or any other known means for attaching two components together. For example, in the case of sleeve 26, the distal tip 26a may be fabricated of metal, such as 304 or 316 stainless steel, which is of course durable, generally corrosion resistant, able to withstand high temperatures, and capable of maintaining the precise tolerances required to ensure alignment of the corresponding optical fiber(s) 30 and/or 38. However, all or a portion of the body 26b may be formed of a different material, such as plastic or the like. In the case where the fluid F is at a relatively high temperature, one advantage of forming the remainder of the body 26b of plastic (or another material having a low thermal conductivity compared to metal) is that the amount of heat transferred to the corresponding enclosure E is reduced. This helps to prevent the heat from interfering with the sensitive electronic components, such as the LED 34 and the photodetector 40. Indeed, the body 26b of the sleeve 26 is preferably elongated (e.g., 3–4 inches long) and, thus, effectively acts to insulate the electronics from heat.

The body 26b may also be provided with recesses or structures for assisting in mounting any electronic components in place and guiding any external power or communication lines. An external annular flange (not shown) may also be provided on the body 26b portion of the sleeve 26 for seating against the corresponding sidewall of the body 16. Fasteners may then be used to secure the flange and, hence, the sleeve 26 to the body 16.

Regardless of the type of sleeve used, if any, the judicious use of seals to also recommended to prevent fluid F from entering the passage(s) 20, 22, or 24 and interfering with the operation of the electronic components. The seals or substances used may be of any type known in the art, such as conventional O-rings or the like fabricated of resilient materials, such as rubber. If desired, seating recesses may be formed in the distal tips 26a, 44a, 58a of the sleeve(s) 26, 44, 58 or portions of the corresponding passage 20, 22, or 24 to receive any seals present.

Obvious modifications or variations are possible in light of the above teachings. For example, while the body 16 is shown as being a solid block of a generally rectangular material, the use of different arrangement is possible, as long as the pocket 14 or a similar cavity or recess is present and the desired sensing configuration (backscatter, transmission, or sidescatter) can be achieved. Also, while three fiber optic units 32, 42, 56 are shown in FIG. 2, it should be appreciated that only a single unit may be provided in a backscatter configuration (in any of the three positions, if available), only two units may be provided in a transmission configuration, or only two units may be provided in a sidescatter configuration. As suggested in the foregoing passage, the body 16 may thus be provided with one, two, or all three passages 20, 22, or 24, as necessary or desired for a particular application. Any of the passages 20, 22, 24 present could also be adapted for directly receiving one or more optical mediums, such as fibers, instead of a separate sleeve (although this would ostensibly limit the ability to easily change the path length in the transmission and sidescatter configurations). Multiple optical fibers may also be used, as necessary or desired for a particularly application. While the drawings show the segment 10 positioned above the body 16, it is also possible and preferred from a sanitary aspect to invert or otherwise reorient the arrangement. This would allow pipe to drain after cleaning. Additionally, use of the apparatus, system, and method on a pipeline P is mentioned, but it should be appreciated that the body 16 including the pocket 14 could be adapted for use with any type of vessel, container, or other structure for holding a fluid. While the focus is on the use of light and optics for detecting or sensing the characteristics of the fluid and is preferred, it is also possible to use the apparatus of the present invention with other types of measuring devices, such as probes used to measure the electrical conductivity of a fluid (i.e., the resistance across a known distance or path length) or others without departing from the broadest aspects of the invention.

In summary, the apparatus of the present invention provides several benefits and advantages as compared to prior art proposals. First, the pocket 14 is out of the main portion of the fluid flow F. Using the present arrangement, alignment of the optical fibers when positioned in a transmission configuration is assured. The ability to decrease the path length and the concomitant small distance reduces the effects of thermal expansion. The pocket 14 also allows for taking backscatter, transmissions, or sidescatter measurements using the same apparatus.

The foregoing description is presented for purposes of illustration and description of the various aspect of the invention. The descriptions are not intended to be exhaustive or to limit the invention to the precise form disclosed. The embodiments described above were chosen to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

The invention claimed is:

1. An apparatus for the intended use in receiving at least one medium for transmitting energy to a fluid, comprising:
    a pipe having an outer wall with an opening formed therein and an inlet for receiving the fluid; and
    a body for positioning adjacent to the opening in the outer wall of the pipe, the body including a pocket for receiving a portion of the fluid passing through the opening, the pocket at least partially defined by a first sidewall having a first passage adapted for receiving at least a portion of the at least one medium;
    whereby energy transmitted through the at least one medium reaches the portion of the fluid entering the pocket.

2. The apparatus according to claim 1, wherein the at least one medium is a first optical fiber for transmitting light from a light source to the fluid in the pocket.

3. The apparatus according to claim 2, wherein the first optical fiber is associated with a first fiber optic unit including the light source and the body includes a first auxiliary passage for receiving one or more transmission lines coupled to the first fiber optic unit.

4. The apparatus according to claim 2, wherein a second passage for receiving at least a portion of a second optical medium is formed in a second sidewall partially defining the pocket, whereby light transmitted by the first optical medium to the portion of the fluid in the pocket is received by the second optical medium.

5. The apparatus according to claim 4, wherein the first and second passages are oriented for positioning the first and second optical mediums in either a transmission configuration or a sidescatter configuration.

6. The apparatus according to claim 4, wherein a third sidewall partially defining the pocket includes a third passage adapted for receiving at least a portion of a third optical medium for receiving light transmitted to the portion of the fluid in the pocket by the first optical medium.

7. The apparatus according to claim 4, wherein the second optical medium is associated with a second fiber optic unit and the body further includes a first auxiliary passage and a second auxiliary passage, each auxiliary passage receiving one or more transmission lines coupled to the corresponding fiber optic unit.

8. The apparatus according to claim 4, wherein the body is a single piece of material, the first and second sidewalls are opposed, and the first and second passages are formed using a single tool during a continuous machining process to ensure proper alignment among the first and second optical mediums.

9. The apparatus according to claim 1, wherein the pocket is partially defined by a generally U-shaped bottom wall for promoting smooth fluid flow.

10. The apparatus of claim 1, wherein the at least one medium is an optical fiber projecting through the passage into the portion of the fluid.

11. A system for detecting an optical characteristic of a fluid flowing through a pipeline, comprising:
    a pipe segment for forming a portion of the pipeline, the segment including an outer wall having an opening for communicating with a pocket for receiving a portion of the fluid flow, the pocket being at least partially defined by a first sidewall having a first passage formed therein;

a light source;

a first optical medium positioned at least partially in the first passage for transmitting light from the light source to the fluid flow in the pocket;

a second optical medium capable of receiving light transmitted through or reflected by the portion of the fluid flow in the pocket; and a detector coupled to the second optical medium.

12. The system according to claim 11, wherein the second optical medium is positioned at least partially in the first passage to create at least a backscatter configuration.

13. The system according to claim 11, wherein the pipe segment further includes a second sidewall partially defining the pocket, the second sidewall including a second passage adapted for at least partially receiving the second optical medium.

14. The system according to claim 13, wherein the first and second signal mediums are oriented in a sidescatter configuration.

15. The system according to claim 13, wherein the first and second optical mediums are oriented in a transmission configuration.

16. The system according to claim 15, wherein the pipe segment includes a third sidewall partially defining the pocket and including a third passage adapted for receiving a third optical medium, the system further including a second detector associated with the third optical medium for detecting light transmitted to the fluid in the pocket, whereby the third optical medium is mounted in a sidescatter configuration.

17. The system according to claim 16, further including a fourth optical medium oriented in a backscatter configuration relative to the first optical medium.

18. The system according to claim 16, wherein the third sidewall is a generally U-shaped bottom wall that promotes the smooth flow of fluid through the pocket.

19. The system according to claim 11, wherein the pocket is formed in a separate piece of material attached directly to the pipe segment over the opening formed therein.

20. The system according to claim 19, wherein the material includes first and second auxiliary passages for receiving one or more transmission lines coupled to first and second fiber optic units associated with the first and second optical mediums, respectively.

21. The system according to claim 11, wherein the first optical medium is held in a first bore formed in a first sleeve adapted for positioning in the first passage.

22. The system according to claim 21, wherein the sleeve includes a distal tip and an oversized body and the passage is adapted for receiving the sleeve such that the distal tip projects into the pocket.

23. The apparatus of claim 11, wherein the first medium and second medium are optical fibers, at least one of which projects through the passage into the portion of the fluid.

24. An apparatus for intended use in characterizing a fluid flowing along a pipeline, comprising:

a pipe segment for forming part of the pipeline, the segment including an inlet, an outlet, and a first sidewall having an opening;

a body carried by the pipe segment and including a pocket for receiving a portion of the fluid passing through the opening, said pocket including a second sidewall having a passage formed therein; and at least one optical fiber at least partially positioned in the passage.

25. The apparatus according to claim 24, wherein the body is attached directly to the pipe.

* * * * *